US005457247A

United States Patent [19]

Klingler et al.

[11] Patent Number: 5,457,247

[45] Date of Patent: Oct. 10, 1995

[54] PROCESS FOR PREPARING (S)- AND (R) -BUT-3-EN-2-OL AND THE DERIVATIVES THEREOF FROM L-OR D-LACTIC ACID ESTERS

[75] Inventors: Franz D. Klingler, Griesheim; Manfred Psiorz, Ingelheim, both of Germany

[73] Assignee: Boehringer Ingelheim KG, Ingelheim am Rhein, Germany

[21] Appl. No.: 361,250

[22] Filed: Dec. 21, 1994

Related U.S. Application Data

[63] Continuation of Ser. No. 75,080, Jun. 10, 1993, abandoned.

[30] Foreign Application Priority Data

Jun. 13, 1992 [DE] Germany .......................... 42 19 510.1

[51] Int. Cl.$^6$ .......................... C07C 29/00; C07C 29/32; C07C 33/02

[52] U.S. Cl. .......................... 568/908; 568/909.5

[58] Field of Search .......................... 568/908

[56] References Cited

U.S. PATENT DOCUMENTS 3,960,977 6/1976 Naf et al. .......................... 568/908

4,118,406 10/1978 Bestmann et al. .......................... 568/878

5,089,659 2/1992 Brueckner et al. .......................... 568/878

FOREIGN PATENT DOCUMENTS 698912 12/1964 Canada .......................... 568/909.5

2436123 5/1980 France .......................... 568/908

2006422 1/1990 Japan .......................... 568/908

*Primary Examiner*—Joseph E. Evans

*Attorney, Agent, or Firm*—R. P. Raymond; M-E. M. Devlin; A. R. Stempel

[57] ABSTRACT

A novel process for preparing enantiomerically pure (S)- or (R)-but-3-en-2-ol compounds includes the following reaction steps:

(a) reacting an alkyl ester of D- or L-lactic acid with a hydropyran compound to obtain a lactate ester having a hydropyranyl ether group, (b) reducing the lactate ester with an aluminum hydride at a temperature below 0° C. to obtain a propionaldehyde having a hydropyranyl ether group, (c) reacting the propionaldehyde with an alkyl phosphonium salt to obtain a 3-butene having a hydropyranyl ether group, and (d) cleaving the hydropyranyl ether group to prepare the enantiomerically pure (S)- or (R)- but-3-en-2-ol.

12 Claims, No Drawings

PROCESS FOR PREPARING (S)- AND (R) -BUT-3-EN-2-OL AND THE DERIVATIVES THEREOF FROM L-OR D-LACTIC ACID ESTERS

This application is a continuation of U.S. patent application Ser. No. 08/075,080, filed Jun. 10, 1993, now abandoned.

The present invention relates to a new process for preparing (S)-and (R)-but-3-en-2-ol (1-buten-3-ol or methylvinylcarbinol) and the derivatives thereof of general formula 1*a* and 1*b*, respectively,

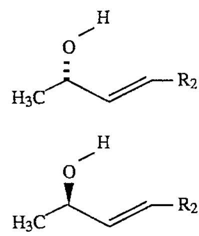

wherein $R_2$ may denote hydrogen and $C_{1-6}$-alkyl, starting from L- and D-lactic acid esters, respectively. $C_{1-6}$-alkyl generally denotes a branched or unbranched hydrocarbon radical having 1 to 6 carbon atoms, which may optionally be substituted by one or more halogen atoms—preferably fluorine—which may be identical to one another or different. The following hydrocarbon radicals are mentioned by way of example: methyl, ethyl, propyl, 1-methylethyl (isopropyl), butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise specified, lower alkyl groups having 1 to 4 carbon atoms, such as methyl, ethyl, propyl, isopropyl, butyl and tert.-butyl are preferred.

Enantiomerically pure butenols are of great importance as synthons for the preparation of enantiomeric secondary products—particularly for the synthesis of pharmaceutical active substances—of 1-buten-3-ols.

Processes for preparing the individual stereoisomers of methylvinylcarbinol are known from the prior art.

Thus, J. Kenyon et al. [J. Kenyon and D. R. Snellgrove, J. Chem. Soc., 1926, 1169] describe a process which makes it possible to obtain S(+)-but-3-en-2-ol, starting from an enantiomer mixture of the methylvinylcarbinol, via the phthalic acid hemiesters thereof and subsequently subjecting them to racemate cleavage by means of brucine and saponification of the desired stereoisomer of the phthalic acid hemiester. The disadvantage of this reaction sequence consists essentially in the fact that numerous crystallisation steps have to be gone through.

In addition, T. Ibrahim et al. [T. Ibrahim, T. J. Grattan and J. S. Whitehurst, J. Chem. Soc. Perkin Trans I, 1990, 3317] describe a process starting from 3-chlorobutan-2-one which is first reduced by means of yeast to the corresponding (2S, 3S)- and (2S,3R)-3-chlorobutan-2-ols. The subsequent etherification with 2-methoxypropene and dehydrohalogenation with potassium tert.-butoxide finally produces the desired (S)(+)-but-3-en-2-ol.

A disadvantage of this reaction sequence is that the reduction with yeast can only be carried out in a very high dilution and consequently the production of a relatively small amount of the butenol requires a relatively large reactor volume.

Furthermore, T. Yoshida et al. [T. Yoshida, M. Kaneoya, M. Uchida and H. Morita, Japanese Published Application 1-132 399 dated 24 May 1989) describe a process for the so-called optical cleaving of (R,S)-2-buten-3-ol in which, after reaction with tributyrine and subsequent enzymatic treatment, the two stereoisomeric butenols can be made available. However, this process suffers from a poor yield and results in products having poor characteristics.

Moreover, G. Giacomelli et al. [G. Giacomelli, A. M. Caporusso and L. Lardicci, Tetrahedron Lett. 22 (1981) 3663] describe the asymmetric reduction of 1-buten-3-one using optically active trialkylalkanes. In the reaction described therein, however, the (R)-1-buten-3-ol can only be obtained in and enantiomeric excess (e.e.) of 7%.

A higher enantiomeric excess is yielded by a reaction described by H. C. Brown et al. [H. C. Brown and G. G. Pai, J. Org. Chem. 50 (1985) 1384] in which 1-buten-3-one is stereoselectively reduced with so-called Alpine-Borane® (B-(3-pinanyl)-9-borabicyclo[3.3.1]nonane). In this way, (R)-1-buten-3-ol can be obtained in an enantiomeric excess (e.e.) of 60% after a reaction time of 5 days, for example, but only in a yield of 30%.

The aim of the present invention is to make (R)- and (S)-3-buten-2-oles—and the derivatives thereof—available in high yields and in a high enantiomeric excess and to develop a process for preparing them which avoids the disadvantages of the processes known from the prior art.

These objectives are achieved by means of the process described hereinafter and illustrated in the Examples, starting from commercially available D- or L-lactic acid alkylesters, the corresponding alkylesters and especially the ethylesters being preferred.

The process according to the invention consists of four reaction steps:

In the first reaction step the free hydroxyl group—for example that of the L-lactic acid ethylester (2)—is protected. Protection is achieved by means of protecting groups known from the prior art which are resistant to reducing agents [T. W. Greene and P. G. M. Wuts, Protective Groups in Organic Synthesis, 2nd Edition, John Wiley & Sons, Inc., New York, 1991, p. 10 ff.]. Preferably the tetrahydropyranyl protecting group is used. The hydroxyl group is protected using the methods which are also known per se from the prior art. In a preferred embodiment the hydroxyl group of the ethyl lactate is etherified in bulk with 3,4-dihydro-2H-pyran in the presence of a catalytic quantity of an acid in a temperature range from −10° to +50° C.

1st step

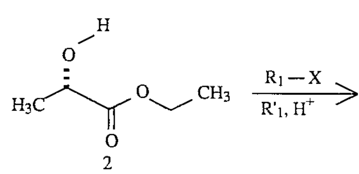

-continued

1st step

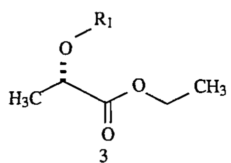

However, the reaction may also be carried out in the presence of a solvent, the suitable solvents including all those which have no detrimental effect on the course of the reaction. Halogenated hydrocarbons such as dichloromethane may be mentioned by way of example.

Preferably, an inorganic acid is used as the acid, hydrochloric acid being particularly preferred. The reaction is carried out in a temperature range from 0° to 40° C.

Then the reaction mixture is fractionally distilled, whilst any solvent present is usefully distilled off beforehand and the lactic acid ester thus protected is isolated.

In the second step of the reaction, reduction of the ethyl lactate prepared in the first reaction step is carried out to produce the corresponding propanal derivative (4), which can also be carried out in accordance with the processes known from the prior art [R. C. Larock, Comprehensive Organic Transformations—A Guide to Functional Group Preparations, VCH-Publishers, Weinheim 1989, p. 621 and loc. cit.]. Preferably the reduction is carried out with optionally complex aluminium hydrides, of which organoaluminium hydrides such as dialkylaluminium hydrides, e.g. diisobutylaluminium hydride (DIBAH) or alkalialkoxyaluminium hydride, and also complex alkali-organoaluminium hydrides such as lithium-tris-(tert.-butoxy)aluminium hydride or sodium-bis-(methoxy-ethoxy)aluminium hydride (Vitride®), are preferred. DIBAH is particularly preferred as reducing agent in the form of a 35% solution in toluene.

2nd step

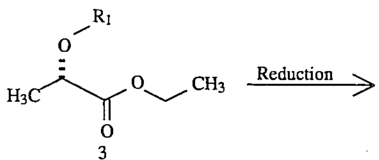

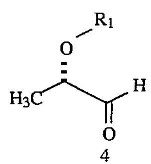

The reduction is preferably carried out in a solvent. Suitable reaction media include all the organic solvents which have no harmful effect on the reduction reaction.

These include, in particular, aliphatic or aromatic hydrocarbons such as petroleum ether, benzene, toluene, xylene, of which toluene is particularly preferred. The reduction is carried out at temperatures below 0° C., preferably in the range from −50° to −20° C. and particularly preferably at −40° C. particularly preferably at −40° C.

For working up, the reaction mixture is first subjected to hydrolysis, preferably using mixtures of lower aliphatic alcohols (such as methanol, ethanol, propanol and isopropanol) and water. It is particularly preferred to use a mixture of 100 parts by volume of water and about 37 parts by volume of methanol at a temperature of −40° C. During hydrolysis, the temperature is also in the ranges specified above. After hydrolysis has ended the reaction mixture is allowed to warm up to ambient temperature (about 20° C.), whereupon the aluminium hydroxide formed during hydrolysis is precipitated as a thick, liquid slurry. The aluminium hydroxide is separated off and the filtrate is evaporated down in vacuo, the residue remaining is fractionally distilled under reduced pressure and the resulting aldehyde (4) thus obtained is isolated.

In the third reaction step the aldehyde (4) is converted into the desired alkene in a Wittig reaction [C. Ferri Reaktionen der organischen Synthese, Georg Thieme Verlag, Stuttgart, 1978, p. 354 and loc. cit.; J. March, Advanced Organic Chemistry, J. Wiley & Sons, New York, 1985, p. 845 and loc. cit.].

3rd step

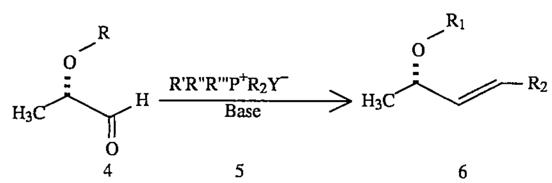

The preparation of the desired phosphonium salts of type (5) - $R_2$=$C_{1-6}$-alkyl—is also known from the prior art. When $R_2$ is methyl as in the working Example, the final product is a but-3-en-2-ol, but when $R_2$ is other than methyl, the final product is more appropriately referred to as an alk-3-en-2-ol. Preferably, alkyltriphenylphosphonium halides are used as so-called Wittig reagents. In order to prepare the alkene the aldehyde is added to a suspension of a solution of the phosphonium salt and a base.

Suitable reaction media include all solvents which do not have a detrimental effect on the course of the reaction, including ethers such as di-n-butylether, glycoldimethylether, diglycoldimethylether, tetrahydrofuran, or sulphoxides such as dimethylsulphoxide or tetrahydrothiophene-1,1-dioxide (sulpholane). It is also possible to use mixtures of the above solvents.

Tetrahydrofuran is particularly preferred as the reaction medium. The bases used are alkali organyls or alkoxyalkali compounds, of which lithium alkyls are preferred. It is particularly preferable to use n-butyllithium in the form of a 15% solution in n-hexane.

The reaction temperature can vary within a wide range, depending on the particular reaction medium used, and is bounded at the bottom end of the range by an insufficient reaction speed and, at the top end of the range, by a preponderance of secondary reactions (e.g. the decomposition of the tetrahydrofuran by the lithium alkyls used as bases).

It has proved advantageous to combine the phosphonium salt and the base at a temperature in the range from 0° to 40° C., the range from 20° to 25° C. being particularly preferred.

The carbonyl compound (4) can also be added within a relatively wide temperature range, whilst it should be mentioned that it has been found advantageous to cool the reaction solution during the addition. A temperature in the range from 0° to 40° C. is preferred, the range from 15° to 20° C. being particularly preferred.

After the reaction has ended the phosphine oxide (or triphenylphosphine oxide) precipitated from the reaction mixture is separated off, e.g. by filtration, the filtrate is evaporated down under reduced pressure and the residue remaining is stirred with water. Then the resulting aqueous suspension is extracted with an organic extraction agent. Suitable extraction agents include solvents which are immiscible with water, of which, in the present case, aliphatic or aromatic hydrocarbons such as branched or unbranched alkanes, benzene, toluene or xylene are preferred. It is particularly preferred to use n-hexane as the extraction agent.

The organic extraction solution is freed from water—optionally with the aid of a desiccant—and after separation of the desiccant it is evaporated down under reduced pressure and the residue is fractionally distilled, again under reduced pressure, and the resulting alkene of type (6) is isolated therefrom.

Since there are a wide range of possible variants in carrying out the Wittig reaction, this makes it possible to choose other reaction media, bases and different reaction conditions, depending on the type of variant selected.

In the fourth and last reaction step the protecting group is cleaved. The individual processes for cleaving the various protecting groups are also known from the prior art. [T. W. Greene and P. G. M. Wuts, Protective Groups in Organic Synthesis, 2nd Edition, J. Wiley & Sons, Inc. New York, 1991, p. 10 ff]. In the process according to the invention the alkene (6) obtained in step 3 is dissolved in a suitable solvent. Suitable solvents, particularly for cleaving the tetrahydropyranyl protecting group, include organic acids such as acetic acid or alcohols such as methanol or ethanol, or polyalcohols, such as ethyleneglycol or glycerol, of which ethyleneglycol is particularly preferred.

4th step

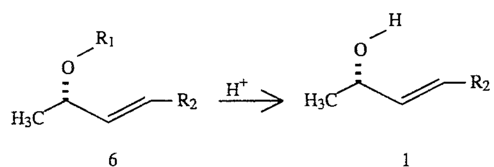

The cleaving is carried out in the presence of an organic acid, organic sulphonic acids being preferred. It is particularly preferable to use p-toluenesulphonic acid.

The reaction temperature may vary within a wide range, depending on the particular reaction medium used, and is bounded at the bottom end solely by too low a reaction speed and, at the top of the range, by the preponderance of secondary reactions.

Preferably, the protecting group is cleaved at a temperature in the range from 0° to 40° C. and, particularly preferably, in the range from 20° to 40° C. and most preferably in the range from 20° to 25° C.

The isolation of the now unprotected alkenol of type (1) can be carried out in various ways, which are familiar to those skilled in the art. If the chemical and physical properties of the reaction product allow, it can be distilled off from the reaction mixture under reduced pressure. When solvents are used-which have a higher boiling point than the alkenol (1) it is also possible first to distil off the reaction medium and then to distil the reaction product, possibly fractionally.

The process described here and in the Examples which follow yields, for example, the S(+)-but-3-en-2-ol in an optical purity of 98.9%.

The objectives mentioned hereinbefore are achieved by means of the processes described in Examples 1–8. Various other embodiments of the process will be apparent from this specification to those skilled in the art. However, it is expressly pointed out that the Examples and the associated description are provided solely for the purposes of illustration and description and should not be regarded as restricting the invention. In particular, it is pointed out that the sequence of synthesis described in the Examples for preparing (S)-but-3-en-2-ol can be transferred to the preparation of the corresponding R-enantiomer.

Similarly, any other desired L- or D-lactic acid alkylester may be used as the starting material.

EXAMPLE

Preparation of S(+)-but-3-en-2-ol

1st step:

608.2 g (97% 5.0 mol) of ethyl L-lactate are placed in a 1.5 liter sulphating apparatus and within 15 minutes 433.0 g (5.0 mol) of 3,4-dihydro-2H-pyran are added with stirring. The temperature falls from 25° C. to 20° C. Then the solution is cooled to 0° C. in a bath of ice/common salt and 4 ml of an ethereal hydrochloric acid solution are added dropwise in 2 minutes. The temperature slowly rises to 12° C. After 30 minutes' stirring, the cooling bath is removed, whereupon the temperature rises to 40° C. within 30 minutes. The solution is stirred for 20 hours at 20°–25° C. Then the reaction solution is fractionally distilled through a column of filler having a mirror coating.

Yield: 882 g of colourless oil (84% of theory) $Bp_{0.4\times10^{2}pa}$: 91° C.

2nd step:

1200 ml of absolute toluene are placed in a 4 liter sulphating apparatus rinsed out with nitrogen and 160 g (0.8 mol) of the tetrahydropyranylether prepared in reaction step 1 are added thereto with stirring. The solution is then cooled with a dry ice/acetone bath to a temperature of –40° C. and within 60 minutes at –40° C. 407 g (1.0 mol) of diisobutylaluminium hydride are added in the form of a 35% solution in toluene. The resulting mixture is then stirred for a further 2 hours at –40° C. The reaction solution is hydrolysed within a period of one hour at a temperature of –40° C. with a solution of 100 ml of distilled water and 36.7 ml of methanol. Then the cooling bath is removed and the reaction mixture is allowed to heat up to ambient temperature. Aluminium hydroxide is precipitated in the form of a thick slurry. It is stirred for 1 hour at a temperature of 25° C. The precipitated aluminium hydroxide is suction filtered over a Seitz-K 400 filter lined with Celite filter clay and is then washed with 3×300 ml of toluene. The filtrate is then evaporated down at 40° C under a pressure of $53.3\times10^2$Pa and the residue is fractionally distilled in vacuo.

Yield: 70 g of colourless oil (55.3% of theory) $BP_{26.6\times10^{2}pa}$: 95°–97° C.

3rd step:

2400 ml of absolute tetrahydrofuran are placed in a 6 liter sulphating apparatus rinsed with $N_2$ and 174 g (0.48 mol) of triphenylmethylphosphonium bromide are added with stirring. The suspension is mixed at ambient temperature, within one hour, with 264 ml (0.53 mol) of a 15% solution of butyllithium in hexane. The suspension dissolves, forming a yellow solution. This is then stirred for a further hour at a temperature of 20°–25° C. Then a solution of 70 g (0.44 mol) of the aldehyde resulting from step 2 in 600 ml of tetrahydrofuran is added dropwise to the Wittig reagent at a temperature in the range from 15°–20° C. (ice cooling) within a period of 90 minutes. The solution decolorises and the resulting triphenylphosphine oxide is obtained in the form of colourless crystals. Stirring is continued for 2 hours at a temperature of 20°–25° C. The triphenylphosphine oxide precipitated is filtered off through a pressure filter lined with Seitz-Filter K 400. The filtrate is evaporated down in vacuo and the residue is stirred with 1 liter of water. Then the suspension is extracted three times, each time with 500 ml of n-hexane. The combined extracts are dried with anhydrous sodium sulphate and, after the desiccant has been filtered off, evaporated down under a pressure of 20 kPa and at 40° C. The residue is fractionally distilled in vacuo (temperature of refrigerator min. 0° C.).

Yield: 34 g of colourless oil (49.6% of theory) $Bp_{26.6\times10^2_{pa}}$: 70°–71° C.

4th step:

In a 250 ml three-necked flask, 34 g (0.22 mol) of the butene derivative isolated in reaction step 3 are dissolved in 110 ml of ethyleneglycol and 4.2 g (22 mMol) of p-toluenesulphonic acid are added. After 2 hours vigorous stirring at 20°–25° C. the S(+)but-3-en-2-ol is distilled off from the reaction solution under a water jet vacuum at a bath temperature of 85° C. and under a pressure of 35 Torr ($46.1\times10^2$Pa). The refrigerator is loaded with coolant at –5° C. 14 g of crude product are isolated which is distilled off under a water jet vacuum using a spiked tubular column.

Yield: 10.2 g of colourless oil (64.4% of theory) $Bp_{80\times10^2_{Pa}}$ 38°–40° C. [α]=D20+31.5° pure d=0.832 optical purity: 98.9% S(+)but-3-en-2-ol 1.1% R(–)but-3-en-2-ol

What is claimed is:

1. A process for preparing enantiomerically pure (S)- or (R)-alk-3-en-2-ol compounds which comprises:

(a) reacting an alkyl ester of D- or L-lactic acid with a 1-hydropyran compound to form a lactate ester having a hydropyranyl ether group in order to protect the hydroxyl of the lactic acid moiety, (b) reducing the lactate ester having a hydropyranyl ether group with an aluminum hydride compound at a temperature below 0° C. to convert the alkoxycarbonyl group to an a aldehyde group to form a propionaldehyde having a 1-hydropyranyl ether group, (c) reacting the propionaldehyde having a hydropyranyl ether group with an alkyl phosphonium salt wittig reagent to form a 3-alkene having a 2-hydropyranyl ether group, and (d) cleaving the hydropyranyl ether group to prepare the enantiomerically pure (S)- or (R)-alk-3-en-2-ol compounds.

2. The process of claim 1 in which the alkyl group of the alkyl ester of D- or L-lactic acid contains from 1 to 6 carbon atoms.

3. The process of claim 2 in which the hydropyran compound is dihydropyran or tetrahydropyran.

4. The process of claim 2 in which the aluminum hydride is an organoaluminum hydride.

5. The process of claim 4 in which the reduction temperature is in the range of from about –20° to about –50° C.

6. The process of claim 5 in which the reduction is carded out in the presence of a solvent selected from the group consisting of aliphatic hydrocarbons and aromatic hydrocarbons.

7. The process of claim 2 in which the cleavage of the hydropyranyl ether group is carried out in the presence of a solvent selected from the group consisting of organic acids, alcohols and polyalcohols.

8. The process of claim 7 in which the cleavage of the hydropyranyl ether group compound is carried out in the presence of an organic sulphonic acid.

9. The process of claim 3 in which the reaction of step (a) is carried out in the presence of an inorganic acid.

10. The process of claim 4 in which the organoaluminum hydride is a dialkyl aluminum hydride.

11. The process of claim 10 in which the dialkyl aluminum hydride is diisobutyl aluminum hydride.

12. The process of claim 1 in which the alkyl phosphonium salt Wittig reagent is triphenyl methyl phosphonium bromide and the enantiomerically pure (s)- or (R)-alk-3-en-2-ol compounds are but-3-en-2-ol compounds.

* * * * *